(12) United States Patent
Stefanchik

(10) Patent No.: US 8,157,727 B2
(45) Date of Patent: Apr. 17, 2012

(54) SURGICAL METHODS AND DEVICES WITH MOVEMENT ASSISTANCE

(75) Inventor: David Stefanchik, Morrow, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 1309 days.

(21) Appl. No.: 11/778,142

(22) Filed: Jul. 16, 2007

(65) Prior Publication Data

US 2009/0023983 A1   Jan. 22, 2009

(51) Int. Cl.
*A61B 1/00* (2006.01)
*A61B 1/015* (2006.01)

(52) U.S. Cl. ............... 600/156; 600/104; 600/106

(58) Field of Classification Search .......... 600/114, 600/104, 106, 156; 604/35, 119, 176, 902
See application file for complete search history.

(56) References Cited

U.S. PATENT DOCUMENTS

| | | | |
|---|---|---|---|
| 982,232 A | 1/1911 | Bartholomew | |
| 2,767,705 A * | 10/1956 | Moore | 600/184 |
| 3,589,356 A | 6/1971 | Silverman | |
| 3,823,720 A * | 7/1974 | Tribble | 604/43 |
| 4,158,916 A * | 6/1979 | Adler | 433/91 |
| 4,834,724 A * | 5/1989 | Geiss et al. | 604/540 |
| 5,127,909 A | 7/1992 | Shichman | |
| 5,235,966 A | 8/1993 | Jamner | |
| 5,259,364 A | 11/1993 | Bob et al. | |
| 5,445,644 A | 8/1995 | Pietrafitta et al. | |
| 5,450,843 A | 9/1995 | Moll et al. | |
| 5,522,795 A | 6/1996 | Green et al. | |
| 5,586,968 A | 12/1996 | Grundl et al. | |
| 5,624,381 A | 4/1997 | Kieturakis | |
| 5,658,307 A | 8/1997 | Exconde | |
| 5,836,913 A | 11/1998 | Orth et al. | |
| 5,885,209 A | 3/1999 | Green | |
| 5,906,591 A * | 5/1999 | Dario et al. | 604/95.03 |

(Continued)

FOREIGN PATENT DOCUMENTS

EP   0 304 380   2/1989

(Continued)

OTHER PUBLICATIONS

European Search Report for EP 08 25 2415, mailed Oct. 31, 2008.

(Continued)

*Primary Examiner* — John P Leubecker
(74) *Attorney, Agent, or Firm* — Nutter McClennen & Fish LLP

(57) ABSTRACT

An endoscopic device and method of use for facilitating movement of an elongate insertion element through a tortuous passageway includes a tissue engaging section having an outer wall with a plurality of openings that communicate with at least one of a source of vacuum and a source of irrigation, and a porous fabric extending over at least a portion of the tissue engaging section. The tissue engaging section can be appended to an accessory channel formed on an outer surface of the elongate insertion element, wherein the central longitudinal axis of the tissue engaging section is offset from a central longitudinal axis of the insertion element, or can be in the form of an elongate helical ribbon disposed around at least a portion of the insertion element. The movement of the device is effected by applying suction to draw tissue to the device, thus straightening the passageway. The suction can be removed or reduced and then the device can be further advanced along the passageway.

17 Claims, 10 Drawing Sheets

U.S. PATENT DOCUMENTS

| | | | |
|---|---|---|---|
| 5,931,845 A | 8/1999 | Amyette | |
| 5,989,230 A * | 11/1999 | Frassica | 604/264 |
| 6,007,521 A | 12/1999 | Bidwell et al. | |
| 6,030,365 A | 2/2000 | Laufer | |
| 6,309,346 B1 * | 10/2001 | Farhadi | 600/114 |
| 6,371,968 B1 | 4/2002 | Kogasaka et al. | |
| 6,517,477 B1 | 2/2003 | Wendlandt | |
| 6,699,179 B2 | 3/2004 | Wendlandt | |
| 6,939,291 B2 * | 9/2005 | Phee Soo Jay et al. | 600/114 |
| 6,971,990 B2 | 12/2005 | Ziegler et al. | |
| 7,189,249 B2 | 3/2007 | Hart et al. | |
| 7,326,173 B2 * | 2/2008 | Guenst et al. | 600/37 |
| 7,476,196 B2 * | 1/2009 | Spence et al. | 600/37 |
| 7,736,372 B2 * | 6/2010 | Reydel et al. | 606/148 |
| 2001/0044595 A1 | 11/2001 | Reydel et al. | |
| 2003/0176884 A1 | 9/2003 | Berrada et al. | |
| 2004/0097996 A1 | 5/2004 | Rabiner et al. | |
| 2004/0138526 A1 * | 7/2004 | Guenst | 600/114 |
| 2004/0143159 A1 * | 7/2004 | Wendlandt | 600/114 |
| 2004/0143281 A1 | 7/2004 | Hart et al. | |
| 2004/0186349 A1 * | 9/2004 | Ewers et al. | 600/114 |
| 2004/0199052 A1 | 10/2004 | Banik et al. | |
| 2005/0171467 A1 * | 8/2005 | Landman | 604/35 |
| 2005/0209506 A1 * | 9/2005 | Butler et al. | 600/114 |
| 2006/0069414 A1 | 3/2006 | Imran et al. | |
| 2006/0100480 A1 * | 5/2006 | Ewers et al. | 600/114 |
| 2006/0184194 A1 | 8/2006 | Pal et al. | |
| 2007/0049904 A1 * | 3/2007 | Deutsch | 604/540 |
| 2007/0118167 A1 | 5/2007 | Hart et al. | |
| 2007/0173687 A1 * | 7/2007 | Shima et al. | 600/106 |
| 2007/0197866 A1 * | 8/2007 | Park | 600/114 |
| 2007/0203393 A1 * | 8/2007 | Stefanchik | 600/106 |
| 2008/0045803 A1 | 2/2008 | Williams et al. | |
| 2008/0242940 A1 | 10/2008 | Stefanchik | |
| 2008/0243164 A1 | 10/2008 | Stefanchik | |
| 2009/0023983 A1 * | 1/2009 | Stefanchik | 600/104 |
| 2009/0248055 A1 | 10/2009 | Spivey et al. | |
| 2010/0228093 A1 * | 9/2010 | Voegele et al. | 600/204 |

FOREIGN PATENT DOCUMENTS

| | | |
|---|---|---|
| EP | 0304380 | 2/1989 |
| EP | 1721561 | 11/2006 |
| EP | 1803389 | 7/2007 |
| WO | 0154565 | 8/2001 |
| WO | 02/19886 | 3/2002 |
| WO | WO-02/19886 | 3/2002 |
| WO | 03039354 | 5/2003 |

OTHER PUBLICATIONS

Chinese Office Action, CN Application No. 200810131610.X, dated, Sep. 2, 2011.

International Search Report for PCT/US2009/038764, mailed Jul. 15, 2009.

* cited by examiner

SURGICAL METHODS AND DEVICES WITH MOVEMENT ASSISTANCE

FIELD OF THE INVENTION

The present invention relates to surgical devices useful for moving tissue and/or effecting movement of device relative to tissue, and particularly through hollow organs in a patient.

BACKGROUND OF THE INVENTION

Many surgical procedures require the movement or dissection of tissue, or the movement of a device relative to tissue. Space constraints as well as the relative remoteness of a distal end of a surgical tool from the surgeon can make it difficult to move tissue, particularly in endoscopic procedures that require surgical instruments to traverse a tortuous pathway though a tubular organ such as the colon. In some surgical procedures, particularly in laparoscopic and endoscopic procedures, movement of the surgical device can be challenging because it is located in a relatively constrained space that is remote from the surgeon. For example, it can be difficult for an endoscope to follow certain curves within the colon. Accordingly, there is a need for devices that conveniently and effectively enable the movement of tissue and/or the movement of surgical tools relative to tissue.

SUMMARY OF THE INVENTION

The present invention provides methods and devices to facilitate the movement of surgical devices through tortuous passageways (e.g., the colon) in the body. In one aspect an endoscopic device comprises an elongate insertion element adapted to be placed within a patient's body. A tissue engaging section is appended to at least a portion of the insertion element, and the tissue engaging section has an outer wall with a plurality of openings formed therein that communicate with a hollow chamber defined by the outer wall. In one embodiment the hollow chamber is configured to communicate with at least one of a vacuum source and an irrigation source. The device may also have a porous fabric extending over at least a portion of the tissue engaging section. The tissue engaging section can be configured to move relative to the insertion section or it can be configured to move only with the insertion section. In one embodiment the insertion section is a surgical tool for placement within the body, such as an endoscope.

In one embodiment the tissue engaging section is an accessory channel that is appended to an endoscope such that it can move independent of the endoscope. In another embodiment the tissue engaging section is a member that is appended to an endoscope, such as in an interference fit, that it is not movable relative to the endoscope.

In another aspect methods of moving a surgical device through a passageway in the body are provided. For example, a method of advancing a surgical instrument through a body lumen can include providing an elongate surgical instrument having an insertion portion that has appended thereto a tissue engaging section having an outer wall with a plurality of openings formed therein. The method further includes inserting the insertion portion into a hollow body lumen having a tortuous path; communicating a vacuum force to the tissue engaging section such that tissue of the body lumen is drawn against the tissue engaging section; releasing the vacuum force and moving the insertion portion within the body lumen; and repeating the steps of communicating the vacuum force, releasing the vacuum force and moving the elongate insertion portion to navigate the elongate insertion portion through the body lumen.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods for moving tissue and/or moving the devices relative to the tissue during a surgical procedure. While the devices and methods disclosed herein can be used in conventional, open surgical procedures, they are particularly useful in minimally invasive surgical procedures, particularly endoscopic procedures. The principles described herein can be applicable to the particular types of tools described herein, and to a variety of other surgical tools having similar functions. In addition, the tools can be used alone in a surgical procedure, or they can be used in conjunction with other devices that facilitate minimally invasive surgical procedures. A particularly useful aspect of the systems and devices disclosed herein is that they enable movement and manipulation of a surgical instrument through a pathway in the body. That is, the invention enables passage of a device through a pathway in the body such that it is able to move relative to the body tissue and pass through regions of the body that can be difficult to traverse, such as tortuous organs like the colon.

The invention is described herein with reference to an endoscope that is to be moved through an organ in the body. However, a person skilled in the art will understand that the invention is applicable to a variety of other surgical tools that must be passed through passageway in the body, such as hollow organs, during a surgical procedure and particularly during minimally invasive surgical procedures such as endoscopic procedures.

A person skilled in the art will appreciate that the present invention has application in conventional endoscopic and open surgical instrumentation as well application in robotic-assisted surgery.

Figure 1:
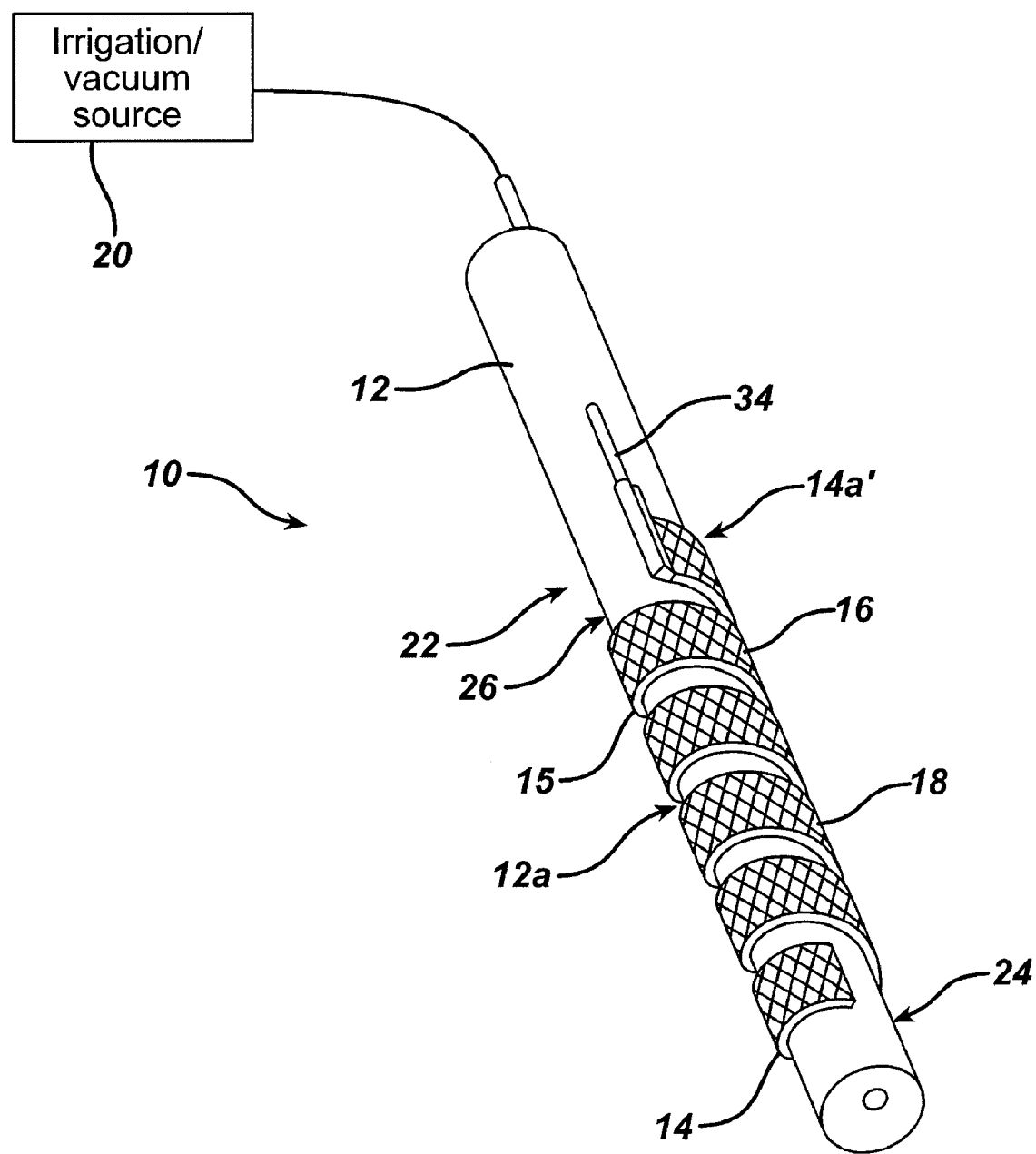
FIG. 1 is a perspective view of a portion of an endoscopic device according to one embodiment of the invention having a stationary tissue engaging section appended thereto and porous fabric covering part of the tissue engaging section.
Figure 2:
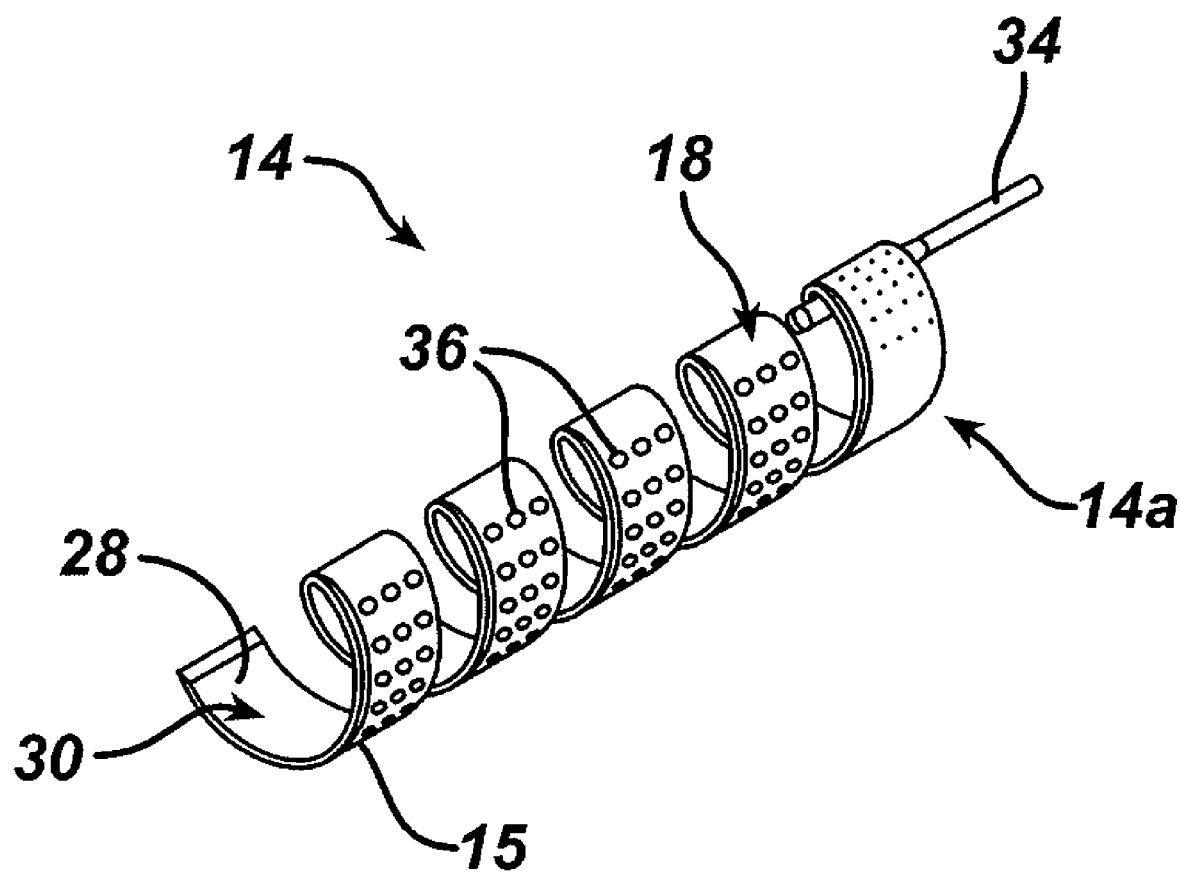
FIG. 2 is a perspective view of a tissue engaging section useful with the endoscopic device of the type shown in FIG. 1.
Figure 3:
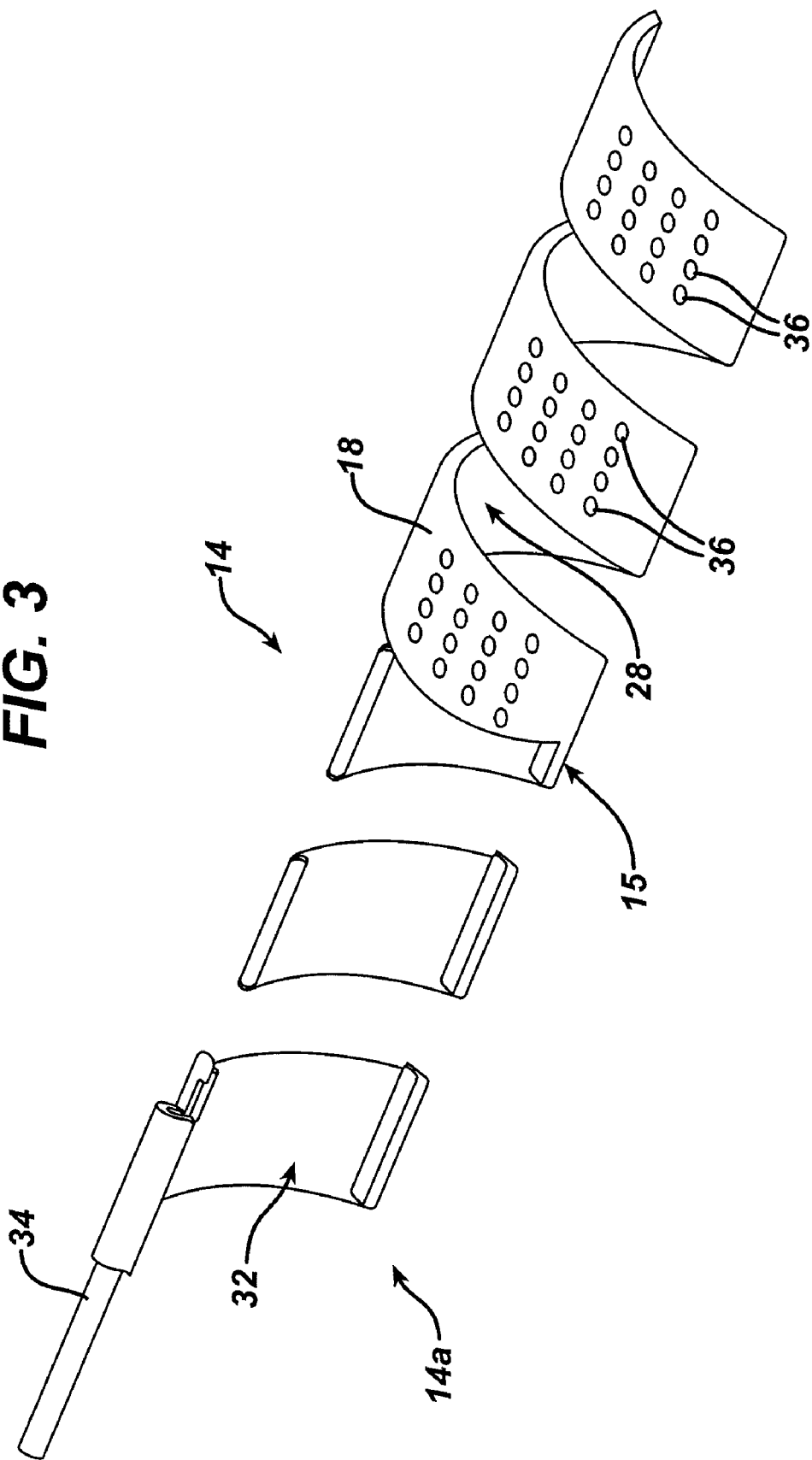
FIG. 3 is a partial sectional view of a portion of a tissue engaging section of the type shown in FIG. 2.

FIGS. 1-3 illustrate one embodiment of a surgical device 10 that is configured to facilitate movement of a surgical instrument relative to tissue. As shown, the device 10 includes an endoscope 12 (only a portion of which is shown) and a tissue engaging section 14 that is appended a distal portion 12a of the endoscope 12. At least a portion of the tissue engaging section 14 includes a porous fabric 16 that covers at least a tissue contacting surface 18 of the tissue engaging section 14. The tissue engaging section 14 can include at its proximal end 14a a conduit 34 that is in communication with an irrigation and/or a vacuum source 20 that can be part of or separate from the endoscope system.

As noted above, the invention is applicable to virtually any surgical tool. In the event that the surgical tool used with the invention is an endoscope is used, it can be any flexible, elongate member that is capable of being inserted into the body, such as through a natural orifice. For example, FIG. 1 shows an insertion portion 22 of an endoscope 12 that is to be inserted into a patient's body, such as through a natural orifice. At least a portion of the endoscope is flexible and the endoscope may have a stearable portion 24 at a distal end thereof.

The tissue engaging section 14 can take the form of virtually any member that can be appended to an outer surface 26 of the endoscope 12. Generally, the tissue engaging section 14 is secured to the endoscope 12 in such a manner that it does not move independent of the endoscope. The tissue engaging section 14 thus can take a variety of forms that enable it to securely fit over the endoscope 12. In an exemplary embodiment, the tissue engaging section 14 is in the form of a helical, ribbon-like member 15 having an outer tissue-contacting surface 18 and an inner tool-contacting surface 28. The helices of the helical member 15 define a central lumen 30 within which the endoscope can seat and be engaged by the tool-contacting surface 28. The outer and inner surfaces 18, 28 of the helical member define a hollow chamber 32 (FIG. 3) that is in fluid communication with an irrigation/vacuum source 20 through conduit 34 that extends proximally from the helical member 15. A plurality of holes 36 can be formed in the tissue contacting surface 18 in fluid communication with the hollow chamber 32 and thus conduit 34 and irrigation/vacuum source 20. Fluid can be passed through conduit 34 and out of holes 36, or a vacuum force can be drawn through the holes 36, as will be explained below.

The helical member 15 can be applied to the endoscope by a variety of techniques that will enable it to remain secured to the endoscope and unable to move independent of the endoscope. In one example, the helical member 15 is appended to the endoscope by an interference fit. This can be effected by forming the helical member 15 from a material that is at least somewhat elastic (e.g., a superelastic alloy or a shape memory material). Moreover, the inner diameter of the lumen 30 when the helical member 15 is in a relaxed condition can be slightly less than the outer diameter of the endoscope 12. A force can be applied to the helical member 15, such as by axially compressing the helical member 15, to increase the inner diameter of the lumen 30. The helical member 15 can then be placed over the endoscope 12 in an appropriate location and the force is removed, allowing the inner diameter of the helical member 15 to decrease and engage the endoscope in an interference fit.

The tissue engaging section 14 can be applied to the endoscope 12 at various appropriate locations. Generally, however, the tissue engaging section 14 is applied at a distal portion of the endoscope 12. In one example, as shown in FIG. 1, the tissue engaging section 14 is applied proximal to the distal most end 38. In one embodiment the tissue engaging section 14 is applied just a proximal to stearable portion 24.

As noted above, a porous fabric 16 extends over at least a portion of the tissue contacting surface 18 of the tissue engaging section 14. The material from which the porous fabric 16 can be made of virtually any material that is biocompatible, having properties that enable an outer surface of the fabric to contact tissue in such a way that there is significant friction between the contact tissue and the fabric and any device over which the fabric is applied. In one embodiment, the fabric material is a porous material such as a mesh material, which can be woven or non-woven. The material from which the mesh is formed can include a variety of synthetic and non-synthetic materials. Examples of synthetic materials include polymers, such as polypropylene, polyethylene, polyester, polytetrafluoroethylene, and nylon. Examples of non-synthetic mesh materials include, but are not limited to silk, cotton, and stainless steel.

Figure 4:
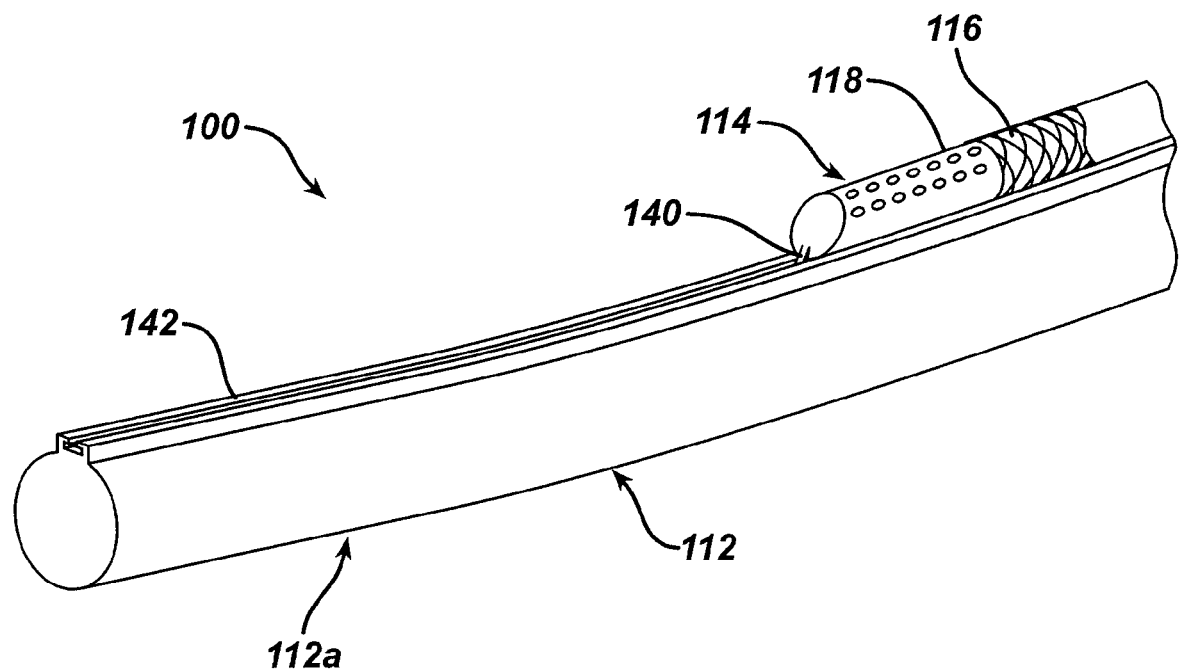
FIG. 4 is a perspective view of a portion of an endoscopic device according to another embodiment of the invention having a movable tissue engaging section appended thereto and porous fabric covering part of the tissue engaging section.
Figure 4A:
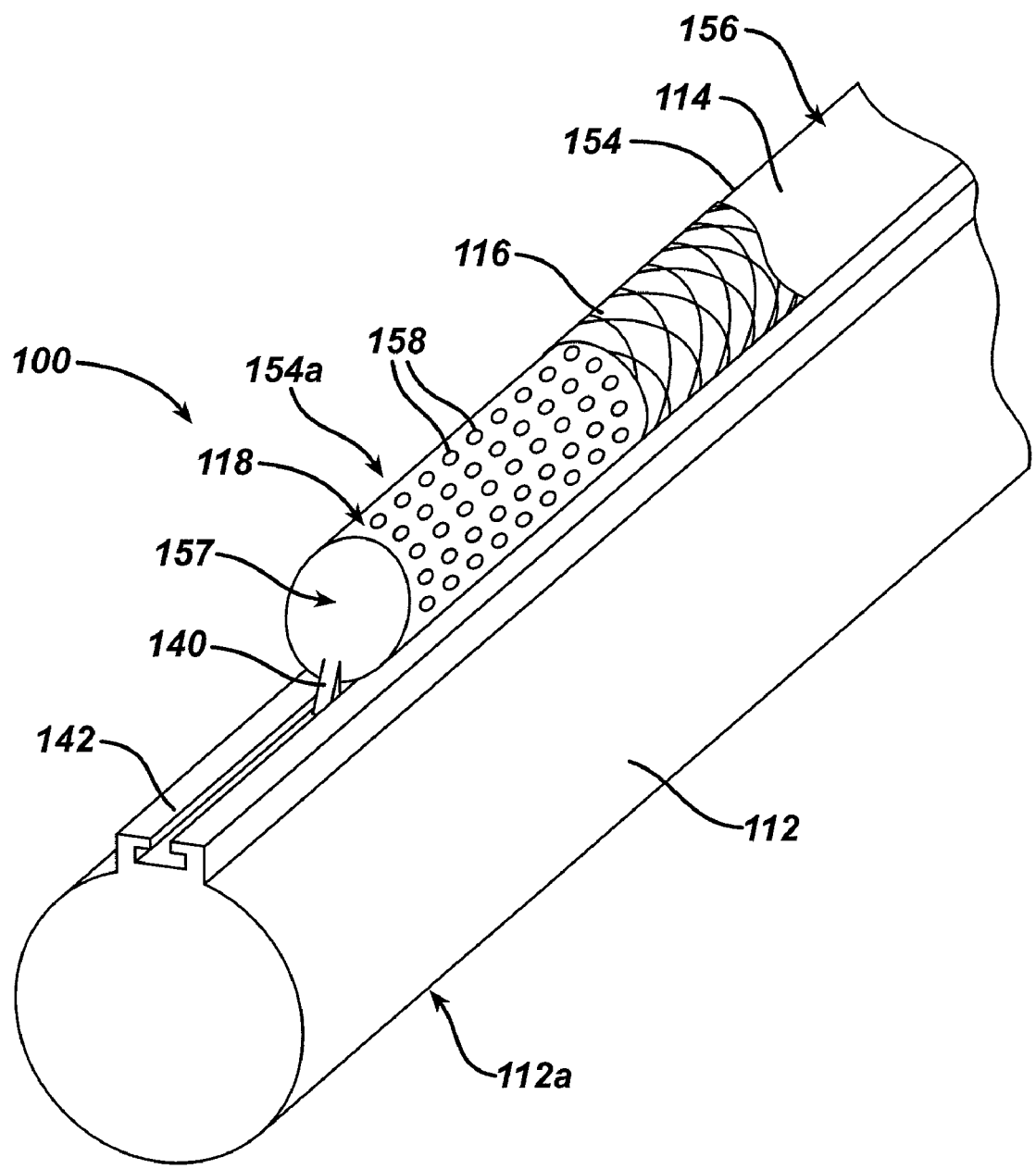
FIG. 4A is a perspective view of the endoscopic device of FIG. 4 with the tissue engaging section in a more distal position.
Figure 5:
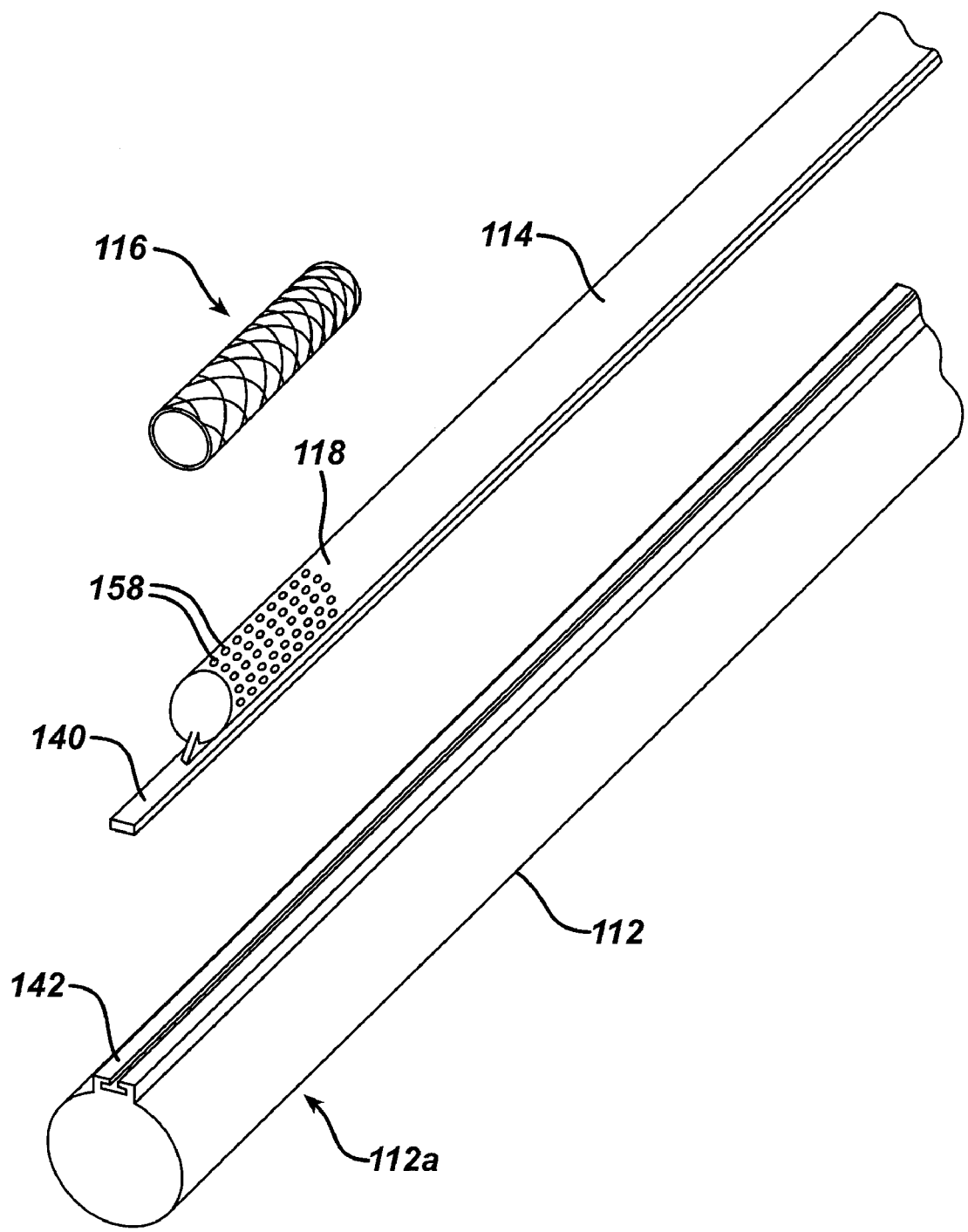
FIG. 5 is an exploded view of the endoscopic device of FIG. 4.

FIGS. 4-5 illustrate another embodiment of a surgical device 100 that is configured to facilitate movement of a surgical instrument relative to tissue. As shown, the device 100 includes an endoscope 112 (only a portion of which is shown) and a tissue engaging section 114 that is appended to a distal portion 112a of the endoscope. As explained below, the tissue engaging section 114 is of a type that is moveable with respect to the endoscope 112. At least a portion of the tissue engaging section 114 includes a porous fabric 116 that covers at least a tissue contacting surface 118 of the tissue engaging section 114. The tissue engaging section 114 includes a mating element 140 that mates with a corresponding mating receptacle 142 on the endoscope to enable the tissue engaging section 114 to engage the endoscope 112 and to move relative to the endoscope. The tissue engaging section 114 may include a proximal end (not shown) or a conduit (not shown) extending from the proximal end that is in fluid communication with an irrigation and/or vacuum source (not shown) that can be part of or separate from the endoscope system.

The endoscope 112 can be of the type described above with respect to FIGS. 1-3. However, as shown in FIGS. 4-5, the endoscope 112 includes a mating receptacle 142 that is configured to mate with a corresponding mating element 140 on the tissue engaging section 114 to enable the tissue engaging section 114 to be appended to the endoscope 112 in such a way that the tissue engaging section and the endoscope are able to move independent of one another. Although illustrated as a female mating receptacle, one skilled in the art will understand that the mating receptacle 142 of the endoscope 112 can alternatively be a male-type member. Similarly, while the mating element of the tissue engaging section is illustrated as a male element it can alternatively be a female element. In the illustrated embodiment, mating receptacle 142 is in the form of a C-shaped channel or track 150 that is configured to receive a complimentary mating element 140 of the tissue engaging section 114, such as a T-shaped member 152.

The tissue engaging section 114 can be in the form of an accessory member 154 that is appended to the endoscope 112 by way of, for example, an accessory channel of an endoscope, in a manner such that it is able to move relative to the endoscope. The accessory member 154 can take a variety of forms. However, like the endoscope, the accessory member 154 can be a thin, elongate and flexible member that is capable of being inserted into a natural orifice of a patient. In one embodiment, as shown in FIGS. 4-5 the accessory member 154 can be a flexible, elongate tubular member having mating element 140 appended to a bottom portion thereof. An outer wall 156 of the accessory member 154 defines a lumen (not shown) that extends within the accessory member 154 and is in fluid communication with an irrigation/vacuum source (not shown) directly or through another conduit (not shown).

A distal end 154a of the accessory member 154 can include a plurality of holes 158 in fluid communication with the lumen (not shown) disposed within the accessory member. In one embodiment, the distal end 157 of the accessory member 154 is closed. The holes 158 are constructed such that fluid can be passed through the accessory member 154 and out of holes 158 or a vacuum force can be drawn through the holes 158 as will be explained below.

As described above with respect to FIGS. 1-3, a fabric 116 can cover a tissue contacting outer surface 156 of the accessory member 154. The 116 fabric can be a mesh material of the type described above with respect to FIGS. 1-3.

One skilled in the art will appreciate that the devices described herein are applicable to a variety of surgical procedures in which a surgical device must be advanced through the body of a patient along a relatively long and potentially tortuous pathway. Exemplary techniques for using the devices described herein will be described in the context of an endoscopic procedure in which an endoscope traverses a portion of the colon.

Figure 6A:
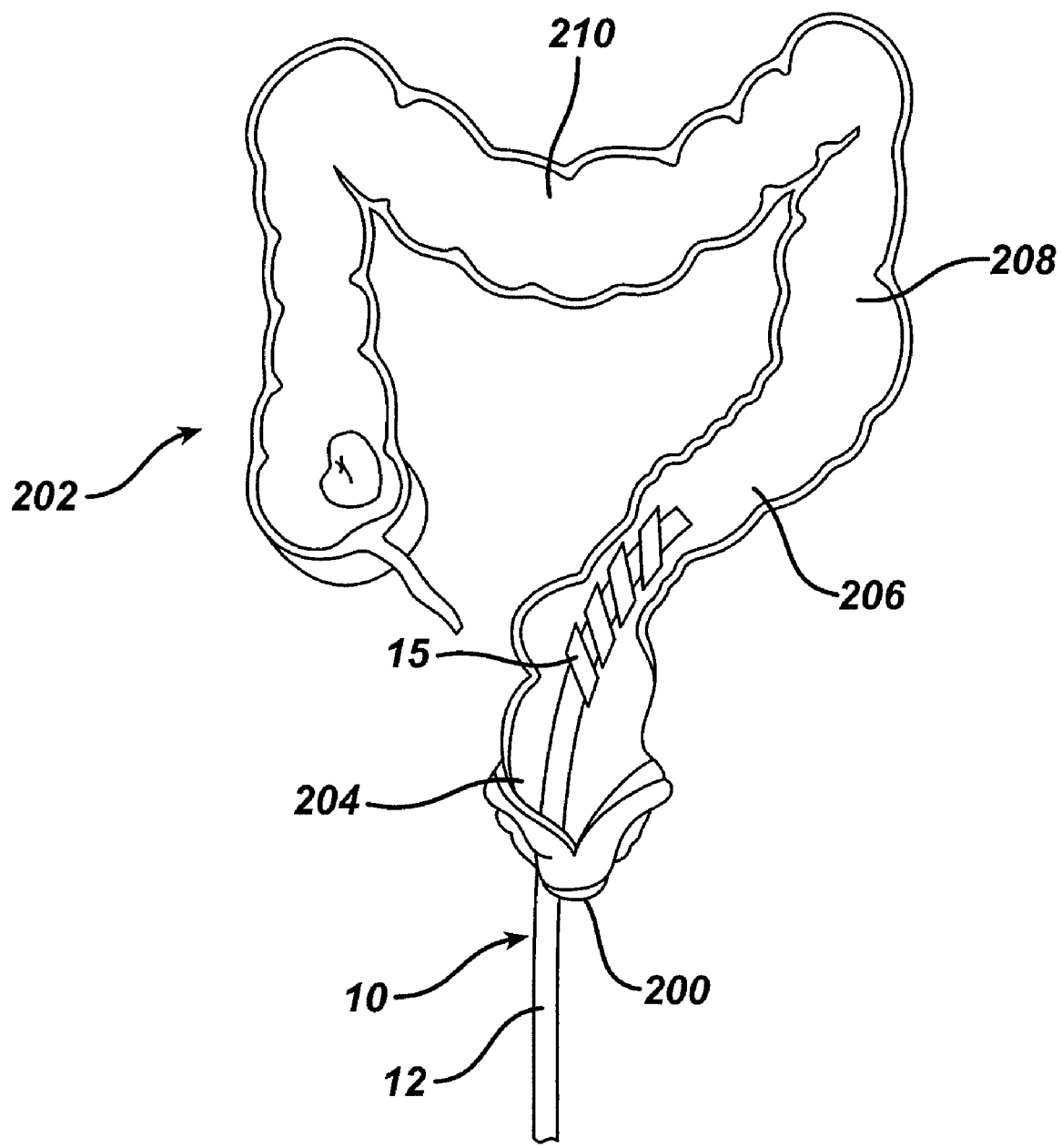
FIG. 6A schematically illustrates an endoscopic device of the type shown in FIG. 1 in a first position in use during an endoscopic procedure.
Figure 6B:
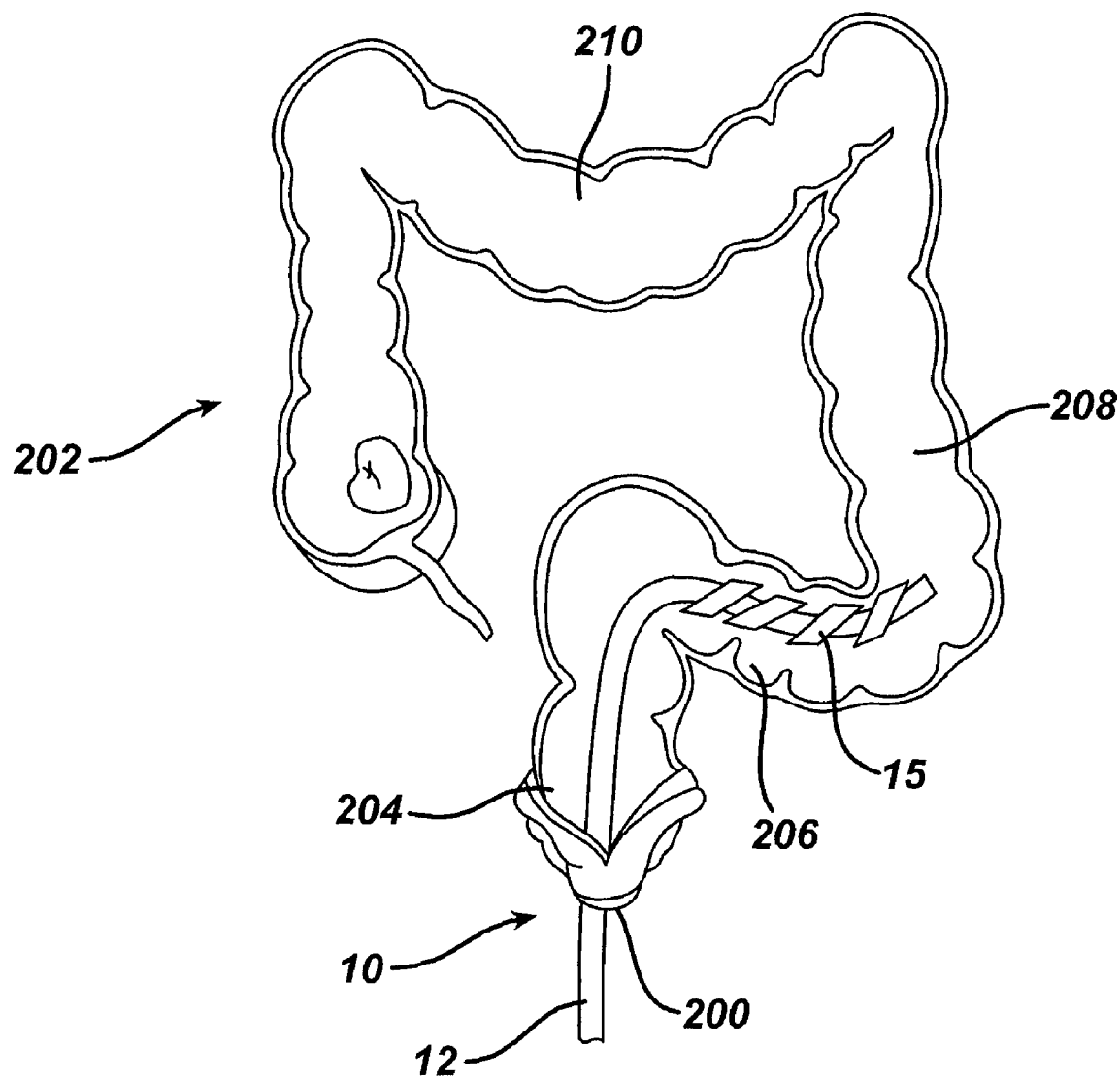
FIG. 6B schematically illustrates an endoscopic device of the type shown in FIG. 1 in a second position in use during an endoscopic procedure.

FIGS. 6A and 6B illustrate the use of a surgical device 10 of the type shown in FIGS. 1-3 in a procedure in which the endoscope 12 enters a patient through the anus 200 and is passed into the colon 202. As shown in FIG. 6A, the endoscope 12 is passed through the rectum 204 which, normally after slightly more than 90° right hand turn, leads to the sigmoid colon 206. Because it can be difficult to maneuver an endoscope through the tortuous pathway leading to the sigmoid colon 206, for example, the surgical device 10 of the invention can assist in this passage. That is, as a turn in the passageway is encountered, tissue tends to bunch up against the distal end of the endoscope, making further distal advancement of the endoscope difficult, particularly when it is necessary to make a turn.

Thus, as shown in FIG. 6A, during passage of an endoscope through the colon, the endoscope encounters a portion of the passageway, e.g., leading to the sigmoid colon 206, that requires a difficult maneuver such as a sharp turn. At this point, using the device 10, suction can be applied to the device, drawing a vacuum through holes 36 in helical member 15 (FIGS. 1-3). The results in tissue being drawn to the helical member 15. Thus, as shown in FIG. 6A, as suction is applied, the drawing of tissue against the helical member 15 causes the normal passageway of the colon in the vicinity of the sigmoid colon 206 to become straighter than normal. (Compare the straightened passageway shown in FIG. 6A in the vicinity of the sigmoid colon 206 to the normal anatomy of the same region shown in FIG. 6B.) The device 10 can assist in what is referred to as the "push-pull" technique, in which a surgeon attempts to hook the colon and then pulls the endoscope back in an attempt to straighten the lumen of the colon. The suction applied by the device 10 aids the surgeon in grasping and maintaining control of the colon rendering the push-pull technique more reliable. Once the passageway is straightened as a result of applying the vacuum force and pulling the endoscope back to straighten the colon, the vacuum can be withdrawn or reduced and, as shown in FIG. 6B, the endoscope 12 is further advanced. Optionally, an irrigation fluid can be passed through holes 36 after the vacuum is withdrawn and during or after advancement of the endoscope 12 to reduce friction between the fabric that covers the helical member and the tissue. The process of applying vacuum force, removing or reducing the vacuum, applying irrigation to reduce friction, and advancing the endoscope can be repeated as necessary as the endoscope is advanced from the descending colon 208 to the transverse colon 210.

Figure 7A:
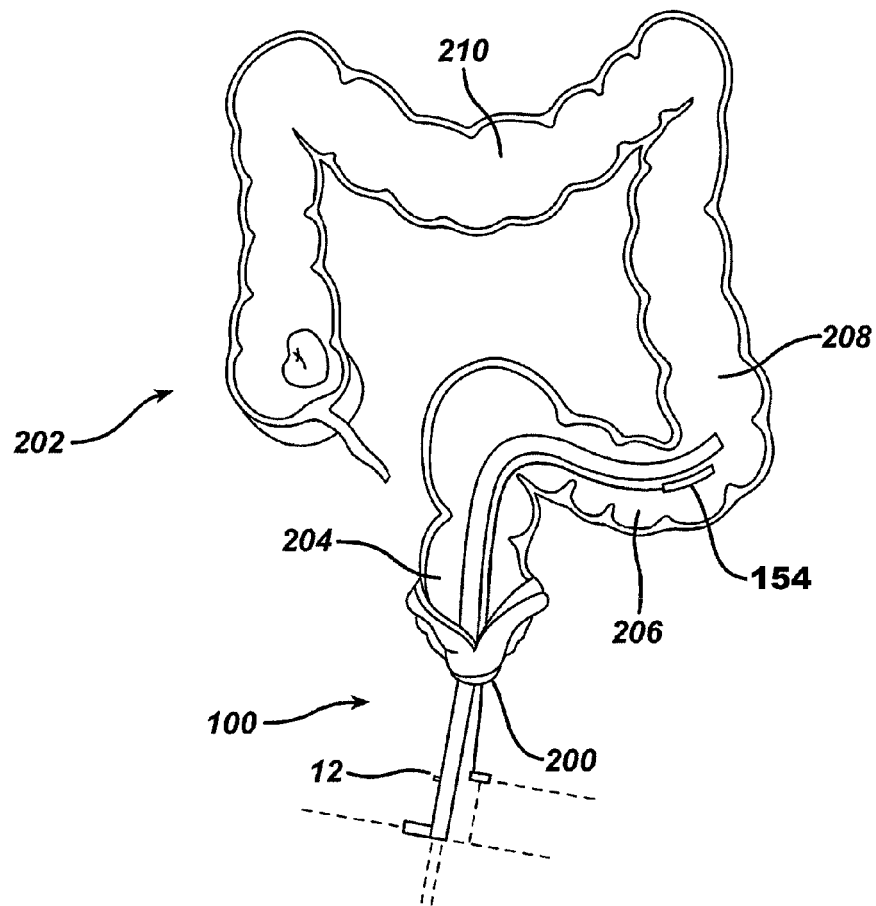
FIG. 7A schematically illustrates an endoscopic device of the type shown in FIG. 4 in a first position in use during an endoscopic procedure.
Figure 7B:
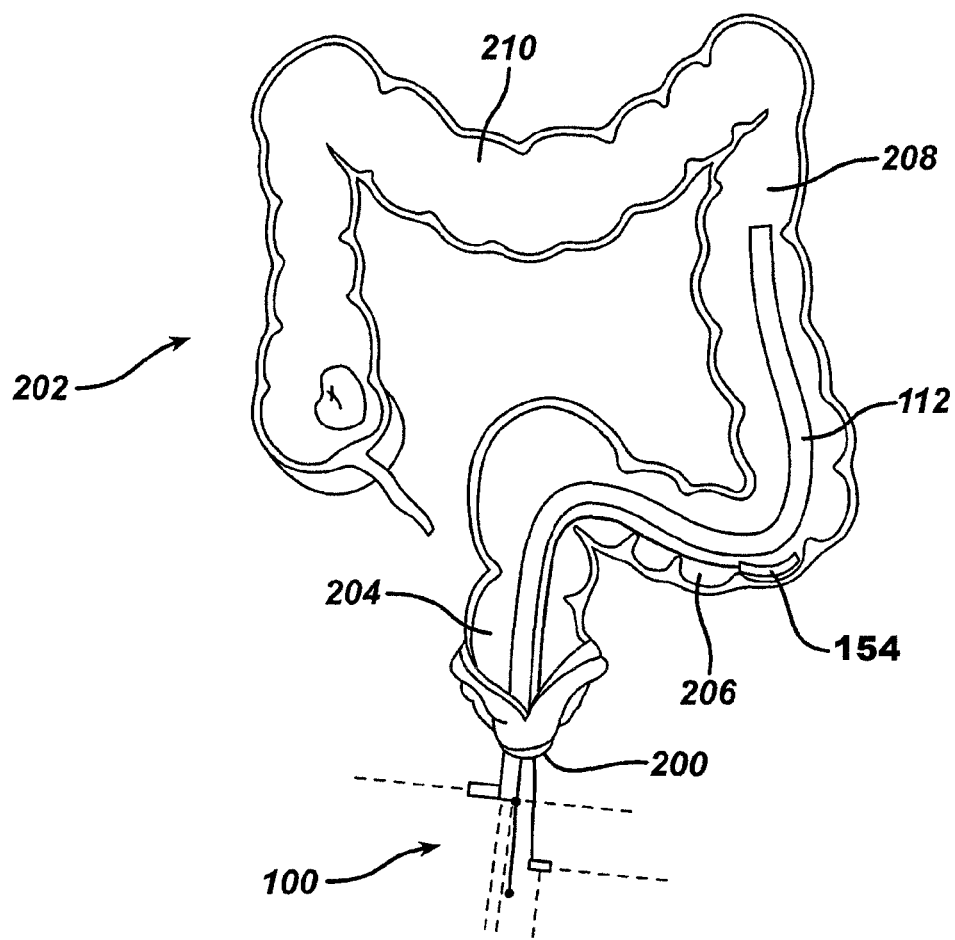
FIG. 7B schematically illustrates an endoscopic device of the type shown in FIG. 4 in a second position in use during an endoscopic procedure.

FIGS. 7A and 7B illustrate the use of a surgical device 100 in a similar surgical procedure that requires passage of an endoscope 112 through the colon 202. Similar to the procedure described above, the endoscope 112 enters the patient through the anus 200 and passes through the rectum 204 into the sigmoid colon 206 as shown in FIG. 7A. At the junction of the sigmoid colon 206 and the descending colon 208, the passageway within the colon becomes tortuous as the colon makes a sharp (greater than 90°) left turn into the descending colon 208. At a juncture such as this, where endoscope advancement becomes difficult as tissue bunches up against the distal end of the endoscope, suction can be applied to the device 100 by drawing a vacuum through accessory member 154, thus anchoring the endoscope to the passageway to some extent. At this point, the endoscope 112 can be advanced distally beyond the accessory member 154 as shown in FIG. 7B. Optionally, an irrigation fluid can be passed through holes 158 in the accessory member 154 after the vacuum is withdrawn and during or after advancement of the endoscope 112. Once the endoscope 112 is advanced beyond the accessory member 154, the accessory member can be advanced distally so that it is approximately adjacent the distal end of the endoscope (such as shown in FIG. 7A). This procedure can be repeated as necessary to advance the endoscope.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An endoscopic device, comprising:
   an elongate insertion element adapted to be placed within a patient's body and comprising an accessory channel formed on an outer surface thereof;
   a tissue engaging section appended to the accessory channel of the insertion element, the tissue engaging section having an outer wall with a plurality of openings formed therein that communicate with a hollow chamber defined by the outer wall,
   wherein the hollow chamber is configured to communicate with at least one of a vacuum source and an irrigation source; and
   a porous fabric extending over at least a portion of the tissue engaging section;
   wherein a central longitudinal axis of the tissue engaging section is offset from a central longitudinal axis of the elongate insertion element.

2. The device of claim 1, wherein the tissue engaging section is configured for movement relative to the elongate insertion element.

3. The device of claim 1, wherein the tissue engaging section is an elongate member that is configured to extend through the accessory channel of the elongate insertion element.

4. The device of claim 3, wherein the accessory channel is a track formed on an outer surface of the elongate insertion element.

5. The device of claim 1, wherein the porous fabric is a mesh material.

6. An endoscopic device, comprising:
   an elongate insertion element adapted to be placed within a patient's body;
   a tissue engaging section in the form of an elongate helical ribbon disposed around at least a portion of the insertion element, the tissue engaging section having an outer surface that defines an outer diameter of the helical ribbon with a plurality of openings formed therein that communicate with a hollow chamber, wherein the hollow chamber is configured to communicate with at least one of a vacuum source and an irrigation source; and
   a porous fabric extending over at least a portion of the tissue engaging section.

7. The device of claim 6, wherein the tissue engaging section is fixed to the elongate insertion element and is not configured for movement independent of the elongate insertion element.

8. The device of claim 7, wherein the helical ribbon includes a conduit extending from a proximal end thereof, the conduit communicating with the hollow chamber and at least one of the vacuum source and the irrigation source.

9. The device of claim 7, wherein the helical ribbon includes an inner surface that defines an inner diameter, the inner surface being configured to surround and contact at least a portion of a distal end of the elongate insertion element in an interference fit.

10. The device of claim 9, wherein the inner diameter of the helical ribbon is selectively variable between a relaxed state in which the inner diameter is less than an outer diameter of the elongate insertion element and an stressed condition in which the inner diameter is greater than an outer diameter of the elongate insertion element.

11. The device of claim 10, wherein the helical ribbon is made of a superelastic alloy or a shape memory material.

12. The device of claim 6, wherein the elongate insertion element is an endoscope.

13. A method of advancing a surgical instrument through a body lumen, comprising:
   providing an elongate surgical instrument having an insertion portion, the insertion portion having appended thereto a tissue engaging section in the form of an elongate helical ribbon and having an outer surface defining an outer diameter of the helical ribbon with a plurality of openings formed therein;
   inserting the insertion portion into a hollow body lumen having a tortuous path;
   communicating a vacuum force to the tissue engaging section such that tissue of the body lumen is drawn against the tissue engaging section;
   releasing the vacuum force and moving the insertion portion within the body lumen; and
   repeating the steps of communicating the vacuum force, releasing the vacuum force and moving the elongate insertion portion to navigate the elongate insertion portion through the body lumen.

14. The method of claim 13, wherein the tissue engaging section is fixed relative to the insertion section.

15. The method of claim 14, further comprising moving the insertion portion proximally within the body lumen while the vacuum force is applied and, following release of the vacuum force, moving the insertion portion distally within the body lumen.

16. The method of claim 14, wherein the step of repeating involves moving the insertion section proximally while the vacuum force is applied and moving the insertion section distally when the vacuum force is withdrawn.

17. The method of claim 13, wherein the surgical instrument is an endoscope.

* * * * *